United States Patent
Mandel et al.

(10) Patent No.: US 6,319,905 B1
(45) Date of Patent: Nov. 20, 2001

(54) METHOD OF CONTROLLING L-DOPA PRODUCTION AND OF TREATING DOPAMINE DEFICIENCY

(75) Inventors: Ronald J. Mandel, Lund (SE); Stuart E. Leff, Alanta, GA (US)

(73) Assignee: Cell Genesys, Inc., Foster City, CA (US)

(*) Notice: Subject to any disclaimer, the term of this patent is extended or adjusted under 35 U.S.C. 154(b) by 0 days.

(21) Appl. No.: 09/314,790

(22) Filed: May 19, 1999

Related U.S. Application Data

(60) Provisional application No. 60/114,016, filed on Dec. 29, 1998.

(51) Int. Cl.[7] .................... A01N 43/04; A01N 63/00; A61K 48/00; C07H 21/04; C12N 15/00
(52) U.S. Cl. .................... 514/44; 424/93.1; 424/93.2; 424/93.6; 435/320.1; 536/23.5
(58) Field of Search .................... 424/93.6, 93.1, 424/93.2; 435/195, 320.1, 328; 514/44; 536/23.5

(56) References Cited

U.S. PATENT DOCUMENTS

| | | | |
|---|---|---|---|
| 4,774,244 | * 9/1988 | Curtius et al. | 514/249 |
| 5,212,082 | 5/1993 | Goldstein et al. | 435/190 |
| 6,040,172 | * 3/2000 | Kaplitt | 435/320.1 |

FOREIGN PATENT DOCUMENTS

| | | |
|---|---|---|
| WO92/07573 | 5/1992 | (WO) |
| WO95/34669 | 12/1995 | (WO) |
| WO96/05319 | 2/1996 | (WO) |
| WO96/39496 | 12/1996 | (WO) |
| WO98/18934 | 5/1998 | (WO) |

OTHER PUBLICATIONS

Verma et al., "Gene therapy—promises, problems and prospects," Nature vol. 389: 239–242, Sep. 1997.*

Anderson W. F., "Human gene therapy." Nature vol. 392: 25–30, Apr. 1998.*

Mandel et al., "Characterization of Intrastriatal Recombinant Adeno–Associated Virus–Mediated Gene Transfer of Human Tryosine Hydroxylase and Human GTP–Cyclohydrolase I in a Rat Model of Parkinson's Disease". The Journal of Neuroscience, vol. 18 (11): 42, Jun. 1, 1998.*

Xu et al., "An expressional study on rat model parkinsonizm by gene therapy". Chinese Medical Journal, vol. 111(2): 154–159, Feb. 1998.*

Wolff et al., "Grafting fibroblasts genetically modified to produce L–dopa in a rat model of Parkinson disease". Proc. Natl Acad. Sci USA, vol. 86: 9011–9014, Nov. 1989.*

Bencsics et al., "Double transduction with GTP cyclohydrolase 1 and Tyrosine Hydroxylase is Necessary for Spontaneous Synthesis of L–DOPA by Primary Fibroblasts". The Journal of Neuroscience, vol. 16(14): 4449–4456, Jul. 15, 1996.*

Uchida et al., "Tetrahydrobiopterin–dependent production of L–DOPA in NRK fibroblasts transfected with tyrosine hydroxylase cDNA: future use for intracerebral grating". Neuroscience Letters, vol. 109: 282–286, 1990.*

Moffat et al., "L–Dope and Dopamine–Producing Gene Cassettes for Gene Therapy Approaches to Parkinson's Disease". Experimental Neurology, vol. 144: 69–73, 1997.*

Ishida et al., "Tetrahydrobiopterin–dependent Production of L–DOPA in Genetically Modified Primary Fibroblasts: Basic Research of Gene Therapy for Parkinson's Disease". Pteridines, vol. 7: 151–153, 1996.*

Miwa et al., "6R–L–erythro–5,6,7,8–Tetrahydrobiopterin and Dopamine Release". Pterdines, vol. 6: 173–180, 1995.*

Ishii et al., "Effect of (6R)–and (6S)–Tetrahydrobiopterin on L–3,4–Dihydroxyphenylalanine (DOPA) Formation in NRK Fibroblasts Transfected with Human Tyrosine Hydroxylase Type 2 cDNA". Neurochem. Int. vol. 17(4): 625–632, 1990.*

Frommel et al., "An estimate on the effect of point mutation and natural selection on the rate of amino acid replacement in proteins." Journal of Molecular Evolution, vol. 21: 233–257, 1985.*

Bowie et al., "Deciphering the message in protein sequences: tolerance to amino acid substitution." Science, vol. 247: 1306–1310, Mar. 1990.*

Ngo et al., "Computational complexity, protein structure prediction, and the Levinthal paradox." The protein Folding Problem and Tertiary Structure Prediction: 491–495, 1994.*

Eck et al., "Gene–Based Therapy." Goodman & Gilman's The Pharmacological Basis of Therapeutics–Ninth Edition, McGraw–Hill: 77–101, 1996.*

A. C. Williams et al., "CFS Hydroxylase Cofactor Levels in Some Neurological Diseases", Journal of Neurology, Neurosurgery, and Psychiatry, 1980, 43, pp. 735–738.

Aminoff, Michael J., *Harrison's Principles of Internal Medicine*, 14th Edition, McGraw–Hill (1998), "Parkinson's Disease and Other Extrapyramidal Disorders", pp. 2356–2359.

(List continued on next page.)

Primary Examiner—Jill D. Martin
Assistant Examiner—Anne-Marie Baker
(74) Attorney, Agent, or Firm—Gates & Cooper LLP

(57) ABSTRACT

The present invention provides an effective approach to achieve the tightly modulated production of L-DOPA and/or dopamine at a preselected target location in the brain of a mammal by combining gene therapy approaches to supply a key enzyme in the synthesis of L-DOPA, and novel drug delivery modalities to administer a uniform level of a modulator of the activity of such key enzyme. The fine-tuned administration of the modulator establishes continuously uniform levels of modulator which in turn allow the effective modulation of L-DOPA and/or dopamine levels at a preselected target location in the brain of the mammal.

15 Claims, 2 Drawing Sheets

OTHER PUBLICATIONS

Hoffer, Barry J. et al., *Trends NeuroScience*, vol. 14, No. 8 (1991), "Ethical issues in brain–cell transplantation", pp. 384–388.

Levine, Robert A. et al., *Science*, vol. 214 (1981), "Treahydrobiopterin in Striatum: Localization in Dopamine Nerve Terminals and Role in Catecholamine Synthesis", pp. 919–921.

Levine, Robert J. et al., *Biochemical and Clinical Apsects of Pteradines*, vol. 2, Walter de Gruyter & Co, (1983), "Recent Advances in Tetrahydrobiopterin Biosynthesis and the Treament of Human Disease", pp. 325–337.

Nagatsu, T. et al., *Neurochemical Research*, vol. 21, No. 2 (1996), "GTP Cyclohydrolase I Gene, Tetrahydrobiopterin, and Tyrosine Hydroxylase Gene: Their Relations to Dystonia and Parkinsonism", pp. 245–250.

Lovenberg, W. et al., *Science*, vol. 204, (May 11, 1979), "Hydrozylase Cofactor Activity in Cerebrospinal Fluid of Normal Subjects and Patients with Parkinson's Disease", pp. 624–626.

Williams, Adrian et al., *The Lancet*, vol. 2, (1979), "Low CSF Hydroxylase Cofactor (Tetrahydrobiopterin) Levels in Inherited Dystonia", pp. 410–411.

LeWitt Ph.D., Peter A. et al., *Neurology 36* (Jun. 1986), "Tetrahydrobiopterin in dystonia: Identification of abnormal metabolism and therapeutic trials", pp. 760–764.

Uchida, Kohichi et al., *Neuroscience Letters*, vol. 109 (1990), "Tetrhydrobiopterin–dependent production of L–DOPA in NRK fibroblasts transfected with tyrosine hydroxylase cDNA; future use of intracerebral grafting", pp. 282–286.

Ishida, Akihiko et al., *Cell Transplantation*, vol. 5 (1996), "Regulation of L–DOPA Production by Genetically Modified Primary Fibroblasts Transfected with Retrovirus Vector System", pp. S5–S7.

Uchida, Kohichi et al., *Dev Neurosci*, vol. 14 (1992), "Tetrahydrobiopterin–Dependent Functional Recovery in 6–Hydroxydopamine–Treated Rats by Intracerebral Grafting of Fibroblasts Transfected with Tyrosine Hydroxylase cDNA", pp. 173–180.

Bencsics, Craig et al., *The Journal of Neuroscience*, 16(14) (Jul. 15, 1996), "Double Transduction with GTP Cyclohydrolase 1 and Tyrosine Hydroxylase is Necessary for Spontaneous Synthesis of L–DOPA by Primary Fibroblasts", pp. 4449–4456.

Mandel, R.J. et al., *The Journal of Neuroscience* 18(11) (Jun. 1, 1998), "Characterization of Intrastriatal Recombinant Adeno–Associated Virus–Mediated Gene Transfer of Human Tyrosine Hydroxylase and Human GTP–Cyclohydrolase 1 in a Rat Model of Parkinson's Disease", pp. 4271–4284.

Moffat, Mark et al., *Experimental Neurology 144* (1997), "L–Dopa and Dopamine–Producing Gene Cassettes for Gene Therapy Approaches to Parkinson's Disease", pp. 69–73.

Wu, Jing et al., *The Journal of Biological Chemistry*, vol. 267, No. 36 (Dec. 25, 1992), "Site–directed Mutagenesis of Tyrosine Hydroxylase", pp. 25754–25758.

O'Malley, Karen L. et al., *Biochemistry 26* (1987), "Isolation and Characterization of the Human Tyrosine Hydroxylase Gene: Identification of 5' Alternative Splice Sites Responsible for Multiple mRNAs", pp. 6910–6914.

Levine, Robert A. et al., *The Journal of Pharmacology and Experimental Therapeutics*, vol. 242, No. 2 (1987), "Entrance of Tetrahydropterin Derivatives in Brain after Peripheral Adminstration: Effect of Biogenic Amine Metabolism", pp. 514–522.

Davis, Michael D., et al, *Proc. Natl. Acad. Sci. USA*, vol. 89 (Nov. 1992), 7–Tetrahydrobiopterin ,"a naturally occurring analogue of tetrahydrobiopterin, is a cofactor for a potential inhibitor of the aromatic amino acid hydroxylases", pp. 10109–10113.

Bigham, E.C. et al., *J. Med. Chem.* vol. 30 (1987), "Synthetic Analogues of Tetrahydrobiopterin with Cofactor Activity for Aromatic Amino Acid Hydroxylases", pp. 40–45.

Williams et al., (1980), *Psychiatry*, vol. 43, pp. 735–738.

Kordower et al., (1998), *Mov. Disorders*, vol. 13, pp. 383–393.

Freed et al., (1992), N.E.J. Med., vol. 327, pp. 1549–1555.

Widner et al., (1992), N.E.J. Med., vol. 327, pp. 1556–1563.

Ranade, (1990), J. Clinical Pharmacol., vol. 30, pp. 871–869.

Schmidt et al., (1983), *Acta Physiol. Scan.*, vol. 522, pp. 19–28.

Naldini et al., (1996), *Science*Vol. 272, pp. 263–267.

Ungerstedt, Arbothnott, (1970) *Brain Res.*, vol. 20, pp. 485–493.

Leff et al., (1998), *Exp. Neurol.*, vol. 151, p. 249–264.

Adams et al., *Principles of Neurology* 4th Ed. McGraw Hill, New York, NY (1989).

Katzung, *Basic & Clinical Pharmacology*, 6th Ed., Appleton & Lange, Norwalk, Ct.

Sambrook et al., *Molecular Cloning: A Laboratory Manual*, 2nd Ed., Cold Spring Harbor Laboratory Press, New York, NY (1989).

Kaufman et al., *Handbook of Molecular and Cellular Methods in Biology and Medicine*, CRC Press, Boca Raton, FL (1995).

McPherson, Ed., *Directed Mutagenesis: A Practical Approach*, IRL Press, Oxford, UK (1991).

*Remington'Pharmaceutical Sciences*, 18th Ed., Genarro, Mack Publishing Co., Easton, PA (1990).

Goeddel, Ed., *Gene Expression Technology: Methods in Enzymology*, vol. 185, Academic Press, Inc., San Diego, CA (1991).

Kaplitt and Loewy, Eds., *Viral Vectors: Gene Therapy and Neuroscience Applications*, Academic Press, San Diego, CA (1995).

Paxinos et al., *The Rat Brain Sterotaxic Coordinates*, 512th Ed. Academic Press, San Diego. CA Robbins, *Gene Therapy Protocols*, Humana Press, Totawa, NJ (1997).

Lemoine and Cooper, *Gene Therapy*, BIOS Scientific Publishers Limited, Oxford, UK (1996).

Kirk, *Experimental Design: Procedures for Behavioral Sciences*, Brooks/Cole Ed., Belmont, CA (1968).

U. S. patent application 08/252,710. Mulligen et al., filed Jun. 2, 1994.

* cited by examiner

METHOD OF CONTROLLING L-DOPA PRODUCTION AND OF TREATING DOPAMINE DEFICIENCY

This application claims the benefit of U.S. provisional application 60/114,016, filed Dec. 29, 1998.

FIELD OF THE INVENTION

This invention relates to the treatment of neurological disorders resulting from dopamine (DA) deficiency. More specifically, this invention relates to methods for the modulation of L-DOPA and/or dopamine levels combining gene therapy approaches to supply a key enzyme in the synthesis of L-DOPA and to novel drug delivery modalities to administer a uniform level of a modulator of the activity of such key enzyme.

BACKGROUND OF THE INVENTION

Parkinson's disease (PD) is a common neurological syndrome characterized by the selective loss of dopaminergic neurons in the nigrostriatal tract. Specifically, dopamine neurons in the substantia nigra degenerate, resulting in the loss of dopamine (3,4-dihydroxyphenethylamine) input to the striatum. Clinically, the reduction of dopamine in the striatum causes several symptoms such as increased muscle rigidity, resting tremor, bradykinesia, and abnormalities of posture and gait. The level of decrease in dopamine synthesis correlates with the severity of the symptoms. Without treatment, PD patients eventually progress to a tragically debilitating rigid state.

Current treatment regimes for PD consist primarily of pharmacological supplementation of the dopaminergic loss with dopamine agonists and levodopa (3-hydroxy-L-tyrosine, L-DOPA), the metabolic precursor of dopamine, which, unlike dopamine, can readily cross the blood-brain barrier (for a general review of PD treatments currently in use see Adams et al., *Principles of Neurology* 4$^{th}$ Ed. McGraw Hill, New York (1989). However, conventional treatments for Parkinson's disease with L-DOPA have proven to be inadequate for many reasons of record in the medical literature. The systemic administration of levodopa, although producing clinically beneficial effects at first, is complicated by the need to reduce dosages that were well tolerated at the outset in order to avoid side effects.

The reason that adverse effects develop in this way is unclear, but selective denervation or drug-induced supersensitivity may be responsible. Some patients also become less responsive to levodopa, so that previously effective doses eventually fail to produce any therapeutic benefit. It is not clear whether this relates to disease progression or to duration of treatment, although the evidence is increasing that disease progression is primarily responsible for the declining response. Responsiveness to levodopa may ultimately be lost completely, perhaps because of the disappearance of dopaminergic nigrostriatal nerve terminals or some pathologic process directly involving the striatal dopamine receptors. For such reasons, the benefits of levodopa treatment often begin to diminish after about 3 or 4 years of therapy irrespective of the initial therapeutic response. In addition, the augmentation of systemic levels of levodopa, necessary to establish therapeutically effective levels at the site of interest, i.e., the brain, have been reported to cause several gastrointestinal adverse effects (including anorexia, nausea and vomiting due to the stimulation of an emetic center located in the brain stem outside the blood-brain barrier), cardiovascular effects (mostly due to the increased catecholamine formation peripherally), dyskinesia, and drastic behavioral effects (depression, anxiety, agitation, insomnia, somnolence, confusion, delusions, hallucinations, psychotic episodes and other changes in mood or personality).

The peripheral administration of levodopa is further complicated by the fact that only about 1–3% of administered levodopa actually enters the brain unaltered, the remainder being metabolized extracerebrally, predominantly by decarboxylation to dopamine, which does not penetrate the blood-brain barrier. This means that levodopa must be given in large amounts when it is used alone. The co-administration of a peripheral dopadecarboxylase has been found to reduce the dosage requirements and some of the side effects, although only marginally. Finally, certain fluctuations in clinical response to levodopa occur with increasing frequency as treatment continues. In some patients, these fluctuations relate to the timing of levodopa intake, and they are then referred to as wearing-off reactions or end-of-dose akinesia. In other instances, fluctuations in clinical state are unrelated to the timing of doses (on-off phenomenon). In the on-off phenomenon, off-periods of marked akinesia alternate over the course of a few hours with on-periods of improved mobility but often marked dyskinesia. (Aminoff, "Parkinson's Disease and other Extrapyramidal Disorders", in Harrison's *Principles of Internal Medicine,* 14$^{th}$ Ed. McGraw-Hill, (1998), pp. 2356–2359), and Katzung *Basic & Clinical Pharmacology,* 6$^{th}$ Ed., Appleton & Lange, Norwalk, Conn.) Thus, there is currently no clearly effective cure for PD.

Since 1987, investigators have grafted primary human fetal cells attempting to supplement nigrostriatal neurons to affected patients. Hoffer et al., (1991) *Trends Neurosci.* 14:384–388) reports that this approach is replete with obstacles including variability in clinical recovery post transplantation, quality control for viral and retroviral contamination problems, nonrenewable sources, and most of all ethical and moral obstacles.

Several laboratories have sought to formulate more effective PD treatment regimens by manipulating a cofactor essential to the activity of tyrosine hydroxylase (TH). Levine et al., (1981) *Science* 214:919–921) teaches that (6R)-5,6,7,8-tetrahydro-L-biopterin ($BH_4$) is localized in dopaminergic nerve terminals in the striatum. The role of $BH_4$ in biogenic amine neurotransmitter metabolism has been extensively studied. As the cofactor for tyrosine and tryptophan hydroxylases, $BH_4$ has been postulated to play a pivotal role in the regulation of biogenic neurotransmitter biosynthesis (see, Levine et al., in *Biochemical and Clinical Aspects of Pteridines,* Vol. 2, pages 325–337, Walter de Gruyter, Berlin (1983) and Nagatsu et al., (1996) *Neur. Res.* 21(2):245–250). $BH_4$ deficiency has been correlated with several diseases including Parkinson's disease (PD) (Lovenberg et al., (1979) *Science* 204:624–626), Alzheimer's disease (Williams et al., (1980) *Psychiatry* 43:735–738), and familial Dystonia (Williams et al., (1979) *Lancet* 2:410–411. Unfortunately, these earlier attempts failed. Le Witt et al., (1986) Neurology 36:760–764, teaches that the main obstacle to the development of therapeutic approaches is that $BH_4$ does not readily cross the blood-brain barrier, and thus peripheral supplementation fails to result in therapeutically effective $BH_4$ concentrations in the cerebral pools.

Gene delivery has been attempted to provide functional copies of the cDNAs encoding proteins necessary for the augmentation of dopamine synthesis. For example, several ex vivo studies have been done using tumorigenic or primary cells expressing rat or human TH. These studies report performing genetic modifications that result in elevated TH gene expression (see for example, PCT Publications WO 96/39496, and WO 98/18934). However, it appears that cells used as vehicles in these studies were consistently deficient in sufficient levels of $BH_4$ cofactor for TH activity. This could be seen in experiments where production of L-DOPA from TH-producing cells in culture was dependent on addition of micromolar to millimolar concentrations of $BH_4$ to the media.

Attempts to augment the production of L-DOPA in TH-producing cells led to the development of methods including the supplementation of $BH_4$. Uchida et al., (1990) *Neuroscience Letters* 109:282–286, and Ishida et al., (1996) *Cell Transplantation* 5:S5–S7, disclose that fibroblasts transfected with various constructs expressing a TH cDNA were able to produce L-DOPA only in the presence of $BH_4$ in the medium. Uchida et al., (supra), and Uchida et al. (1992) *Dev. Neurosci.* 14:173–180 reported that administration of $BH_4$ through a microdialysis probe greatly enhances or enables measurement of in vivo L-DOPA, DA and metabolites in intracerebrally grafted fibroblasts. Unfortunately, these in vivo experiments do not have therapeutic applications since the direct administration of $BH_4$ to the brain is clinically impossible More recently, efforts have been directed to the introduction of both GTP cyclohydrolase, an enzyme critical for $BH_4$ synthesis, and TH to supply both $BH_4$ and TH. Bencsics et al., (1996) *J. Neurosci.* 16(14):4449–4456) teaches the production of dopamine in co-transfected fibroblasts. Similarly, PCT publication WO 96/05319 discloses the transfection of two or more constructs to provide $BH_4$ as well as TH. More recently, Mandel et al., (1998) *J. Neurosci.* 18(11):4271–4284 reported in vivo production of dopamine in a rat model of PD by intrastriatal adeno-associated virus gene transfer of GTP cyclohydrolase and TH (see also PCT publication WO 97/1831). Unfortunately, despite these recent successes, from a clinical perspective much work remains to be done. In a clinical setting, it is often necessary to modulate the production of L-DOPA and dopamine to address a particular patient's requirements, as is the case with any pharmacologic treatment. Furthermore, clinical requirements include the need to target specific tissues to the exclusion of others to avoid the serious side effects discussed above. None of these systems allows the external modulation of the level of L-DOPA and of dopamine expression. Moreover, none of the currently available methodologies provide protocols achieving localized L-DOPA production. The coordination of drug delivery with gene therapy as a treatment, which must also meet both clinical and FDA safety parameters, adds an entire novel dimension to the applicability of this work.

Thus, a great need exists for more effective and versatile gene delivery approaches to modulate striatal L-DOPA and/or dopamine production in a clinically safer and therapeutically effective fashion. Such methods should allow the manipulation of TH activity to address each patient's requirements, such as the stage of neuronal degeneration, the age and condition of the patient, interactions with other medications taken by the patient, side-effects, and the like. It is to this end that this invention is directed.

SUMMARY OF THE INVENTION

The inventors have discovered that the peripheral continuously regulated administration of a modulator to a transgenic cell expressing a key enzyme in the synthesis of L-DOPA, at a preselected target location, allows a surprisingly effective approach to modulate striatal L-DOPA and/or dopamine production. This discovery has been exploited to develop the present invention, which includes clinically safer, more effective and versatile methods to augment L-DOPA and/or dopamine production for therapeutic purposes at a preselected target location.

The present invention provides an effective approach to achieve the tight modulation of striatal L-DOPA and/or dopamine levels by combining gene therapy approaches to supply a key enzyme in the synthesis of L-DOPA, at a preselected target location, and novel drug delivery modalities to administer peripherally a uniform level of a modulator of the activity of such key enzyme. The fine-tuned administration of the modulator establishes continuously uniform levels of modulator which in turn allow the effective modulation of striatal L-DOPA and/or dopamine levels in the mammal.

In a first aspect, the invention provides a method for the external modulation of striatal L-DOPA and/or dopamine levels in a mammal by introducing a polynucleotide encoding a key enzyme in the synthesis of L-DOPA at a preselected target location in the brain of the mammal, and by the fine-tuned peripheral administration of a modulator to establish continuously uniform levels of the modulator. Such fine-tuned, continuously adjusting peripheral administration allows the effective modulation of L-DOPA and/or dopamine levels in the mammal. As it will be apparent hereinafter, the invention provides clinically safer, more effective and versatile methods for the treatment of a mammal suffering from a dopamine deficiency such as, for example, Parkinson's disease (PD).

In some embodiments of the invention the introduced polynucleotide encodes tyrosine hydroxylase, or a functional derivative or a functional equivalent of tyrosine hydroxylase, capable of enzymatically converting tyrosine to L-DOPA. In one embodiment, the polynucleotide encoding a key enzyme in the synthesis of L-DOPA is administered at a preselected target location. In another embodiment of the invention, the externally controllable modulator is tetrahydrobiopterin ($BH_4$), tetrahydropterin ($PH_4$), or a derivative thereof. Representative nonlimiting examples of modulators according to the invention include $BH_4$, $PH_4$, 6-$MPH_4$, 6,6-$MPH_4$, 6,7-$MPH_4$, dihydrosepiapterin, 7-$BH_4$, $NH_4$, 6-$CPH_4$, 6-$PPH_4$, 6-$MMPH_4$, and 6-$EMPH_4$. Fine-tuned peripheral administration of the modulator to establish continuously uniform levels of modulator is effected by adjusting the rate of flow of the modulator introduced into the body of the mammal. In some preferred embodiments of the invention such fine-tuned administration is achieved using commercially available implantable infusion pumps, such as a continuous minipump, which may be programmed from outside the body via telemetry.

In a second aspect, the present invention provides a method for the evaluation of the effects of varying concentration of L-DOPA and/or dopamine at a preselected target location in the brain of a mammal. More specifically, the methods according to this second aspect of the invention provide the tools necessary for the analysis of the neuroprotective potential and physiological effects of precisely regulated levels of L-DOPA and/or dopamine.

BRIEF DESCRIPTION OF THE DRAWINGS

The foregoing and other objects of the present invention, the various features thereof, as well as the invention itself, may be more fully understood from the following description, when read together with the accompanying drawings in which.

DETAILED DESCRIPTION OF THE PREFERRED EMBODIMENTS

Figure 1:
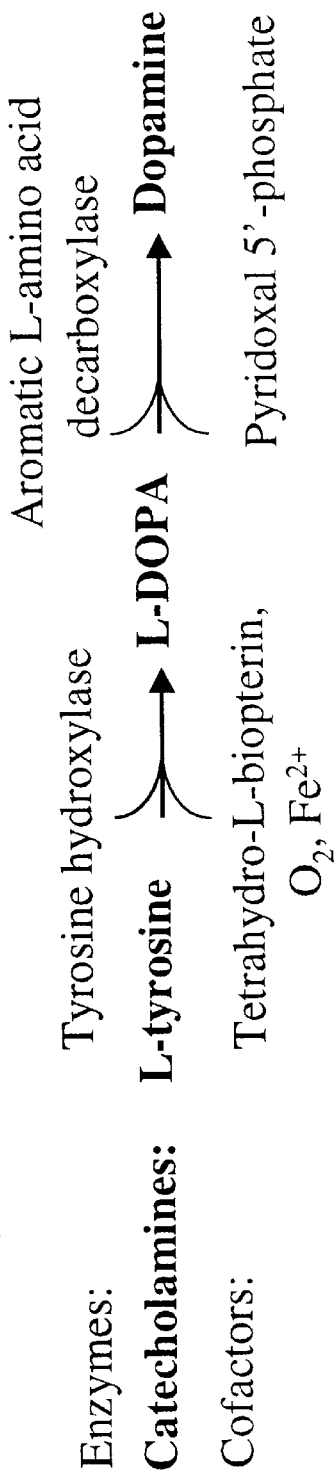
FIG. 1 is a diagrammatic representation of the dopamine biosynthesis pathway showing the role of tyrosine hydroxylase in the conversion of L-tyrosine to L-DOPA.
Figure 2:
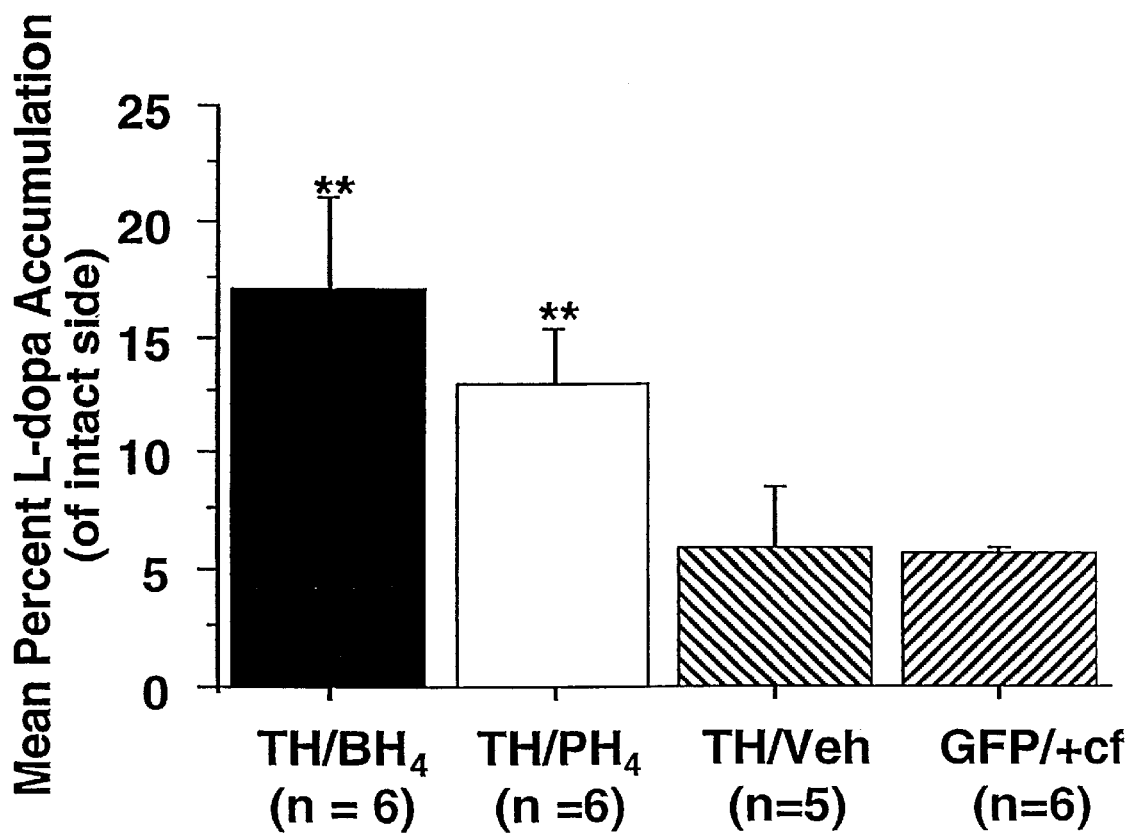
FIG. 2 is a graphic representation showing the ability of the methods of the invention to enhance tyrosine hydroxylase activity. Closed bars represent data from $BH_4$ concentration experiments while open bars represent data from $PH_4$ concentration experiments as indicated on the legend. Peripheral $BH_4$ and $PH_4$ are demonstrated to increase L-DOPA levels in striatal cells that are transduced with a recombinant lentivirus and are expressing the human tyrosine hydroxylase enzyme. The experimental groups are indicated under the appropriate bar. TH or green flourescent protein (GFP) indicates whether a group received lenti-hTH or lenti-GFP, respectively; $BH_4$, $PH_4$, Veh and +cf refer to the peripheral injection regimen that each group received, i.e., $BH_4$ (closed bar+SEM), $PH_4$ (open bar+SEM), vehicle (left hatched bar+SEM), and the lenti-GFP group which received co-factor treatment (+cf, right hatched bar+SEM) which consisted of both $BH_4$ (n=3) and $PH_4$ (n=3) administration. The 'n' numbers of each group are indicated under the appropriate bar. The double asterisks indicate statistical significance as compared to both control groups.

The patent and scientific literature referred to herein establishes the knowledge that is available to those with skill in the art. The issued U.S. patents, allowed patent applications, and articles cited herein are hereby incorporated by reference in their entirety.

The inventors have made the unexpected discovery that the continuous regulated peripheral administration of a modulator, establishing a uniform concentration of the modulator, allows a surprisingly effective approach to modulate L-DOPA and/or dopamine production in a transgenic cell expressing a key enzyme in the synthesis of L-DOPA and/or dopamine at a preselected target location for transfer to the striatum.

The present invention thus provides an effective approach to achieve the tightly modulated production of striatal L-DOPA and/or dopamine levels at a preselected target location in a mammal. The invention achieves this result by combining gene therapy approaches to supply a key enzyme in the synthesis of L-DOPA and/or dopamine, and novel drug delivery modalities to administer a uniform level of a modulator of the activity of such key enzyme. The fine-tuned peripheral administration of the modulator establishes continuously uniform levels of modulator which in turn allow the effective modulation of L-DOPA and/or dopamine levels at a preselected target location in a mammal. The invention thus, provides clinically safer, more effective and versatile methods for the modulation and for the augmentation of L-DOPA and/or dopamine production for therapeutic purposes. Finally, the invention provides a novel approach to the evaluation of the effects of varying concentration of L-DOPA and/or dopamine at a preselected target location in the brain of a mammal. More specifically, the methods according to this second aspect of the invention provide the tools necessary for the analysis of the neuroprotective potential and physiological effects of precisely regulated levels of L-DOPA and/or dopamine.

Technical and scientific terms used herein have the meanings commonly understood by one of ordinary skill in the art to which the present invention pertains, unless otherwise defined. Reference is made herein to various methodologies known to those of skill in the art. Standard reference works setting forth the general principles of recombinant DNA technology include Sambrook, et al., *Molecular Cloning: A Laboratory Manual*, $2^{nd}$ Ed., Cold Spring Harbor Laboratory Press, New York (1989); Kaufman, et al., Eds., *Handbook of Molecular and Cellular Methods in Biology and Medicine*, CRC Press, Boca Raton (1995); McPherson, Ed., *Directed Mutagenesis: A Practical Approach*, IRL Press, Oxford (1991).

Any suitable materials and/or methods known to those of skill can be utilized in carrying out the present invention. However, preferred materials and/or methods are described. Materials, reagents and the like to which reference is made in the following description and examples are obtainable from commercial sources, unless otherwise noted.

In the description that follows, a number of terms used in recombinant DNA technology are extensively utilized. In order to provide a clear and consistent understanding of the specification and claims, including the scope to be given such terms, the following definitions are provided.

A "polynucleotide," as is generally understood and used herein, refers to a polymer of nucleoside, and includes but should not be limited to DNA, cDNA, RNA and analogs thereof.

The term "recombinant DNA" means any recombinant DNA molecule formed by joining DNA segments from different sources and produced using recombinant DNA technology (i.e., molecular genetic engineering). A "DNA segment", as is generally understood and used herein, refers to a molecule comprising a linear stretch of nucleosides wherein the nucleosides are present in a sequence that can encode, through the genetic code, a molecule comprising a linear sequence of amino acid residues that is referred to as a protein, a protein fragment or a polypeptide.

The term "gene" is a DNA sequence related to a single polypeptide chain or protein, and as used herein includes the 5' and 3' untranslated ends. The polypeptide can be encoded by a full-length sequence or any portion of the coding sequence, so long as the functional activity of the protein is retained.

The term "complementary DNA" also referred to as "cDNA" refers to a recombinant nucleic acid molecule synthesized by reverse transcription of messenger RNA ("mRNA").

An "expression vector" is a vehicle, including a cloning vector which is capable of expressing a gene which has been cloned into it, after introduction into a host cell.

A "functional equivalent" of a biochemical moiety, either protein or polynucleotide, is a molecule that possesses a biological activity (either functional or structural) that is substantially similar to a biological activity of the protein or polynucleotide sequence of which it is said to be a functional equivalent. The term "functional equivalent" includes functional derivatives of a protein and may contain post-translational modifications such as covalently linked carbohydrate, depending on the necessity of such modifications for the performance of a specific function. Accordingly, a functional equivalent may contain additional chemical moieties not normally a part of the molecule to which it is a functional equivalent. Such moieties can improve the molecule's solubility, absorption, biological half life, pharmacokinetic absorption and adsorption, and the like. The moieties can alternatively decrease the toxicity of the molecule, eliminate or attenuate any undesirable side effect of the molecule, and the like. Moieties capable of mediating such effects are disclosed in *Remington's Phar-* maceutical Sciences 18$^{th}$ Ed., Gennaro, Mack Publishing Co., Easton, Pa. (1990). Procedures for coupling such moieties to a molecule are well known in the art.

The term "functional derivative" is intended to include the "fragments," "segments," "variants," "analogs," or "chemical derivatives" of a molecule. A "variant" of a protein or polynucleotide is meant to refer to a molecule substantially similar in structure and biological activity to either the protein or polynucleotide. Thus, provided that two molecules possess a common activity and can substitute for each other, they are considered variants as that term is used herein even if the composition or secondary, tertiary, or quaternary structure of one of the molecules is not identical to that found in the other, or if the amino acid or nucleotide sequence is not identical.

The term "transfection" is used to mean the introduction by physical means of an exogenous nucleic acid into a cell. The terms "transduction" and "infection" are used herein interchangeably to mean the introduction of an exogenous nucleic acid in a viral vector, preferably a genetically engineered viral vector occurring as a viral particle. The term "introduction" is used interchangeably to mean either transfection, transduction, or infection. For various techniques for manipulating mammalian cells, see Keown et al., (1990) Methods of Enzymology 185:527–537.

In a first aspect, the invention provides a method for the external modulation of striatal L-DOPA and/or dopamine levels in a mammal following introduction of a polynucleotide encoding a key enzyme in the synthesis of L-DOPA at a preselected target location, by peripherally administering to the mammal calibrated dosages of a modulator of the activity of the key enzyme. The fine-tuned peripheral administration of the modulator according to the invention is under external control, allowing one of ordinary skill in the art to establish continuously uniform levels of the modulator at the preselected target location. External control of the modulator levels allows the effective modulation and creation of consistent brain, and preferably striatal, L-DOPA and/or dopamine in the mammal. As it will become apparent below, the ability to establish uniform levels of modulator under external control allows the investigator and/or the clinician to maintain constant levels of L-DOPA and dopamine at a preselected target location, or in the alternative to alter such levels to meet an individual's clinical requirements.

The methods of the present invention are intended for use with any mammal which may experience the benefits of the methods of the invention. Foremost among such mammals are humans, although the invention is not intended to be so limited, and is also applicable to veterinary uses.

Preferably, the mammal is a patient having a disease characterized by dopamine production deficiency. The most common disease characterized by a dopamine production deficiency is PD; however, the subject invention may be readily adapted for the treatment of other diseases characterized by insufficiency of dopamine production.

The terms "treatment" or "treating" as used herein with reference to a dopamine production deficiency disease refer to prophylaxis and to the amelioration of symptoms already present in an individual by either increasing or otherwise modulating striatal L-DOPA and/or dopamine levels. It will be appreciated by the person of ordinary skill in the art that a treatment need not be completely effective from preventing the onset of a disease or inducing the symptoms associated with the disease, nor does a treatment need to cure a disease in order to be effective. Any reduction in the severity of the symptoms, delay in the onset of symptoms, or delay in the rate of progression of severity of symptoms is desirable to a patient. The persons at risk of developing a dopamine production deficiency disease, such as PD, may be treated prophylactically based on any variety of factors suggesting the possible onset of the disease, e.g., family history, environmental exposure to toxins, genetic markers, early symptoms, and the like.

A "key enzyme in the synthesis of L-DOPA" is an enzyme capable of catalyzing the rate-limiting step of catecholamine synthesis, converting the essential amino acid tyrosine to L-DOPA. The anabolic pathway for dopamine production is a two step process (see FIG. 1). In the first step, L-tyrosine is converted to L-DOPA by tyrosine hydroxylase (TH). In the second step, L-DOPA is converted to dopamine by L-amino acid decarboxylase. Preferably, the key enzyme in the synthesis of dopamine is tyrosine hydroxylase or an analog of tyrosine hydroxylase capable of enzymatically converting tyrosine to L-DOPA in the presence of $BH_4$, $O_2$, and $Fe^{2+}$. The term "tyrosine hydroxylase" (TH) as used herein refers to any of a variety of enzymes and functional derivatives thereof having the ability to catalyze the conversion of tyrosine to L-DOPA. Tyrosine hydroxylase has the enzyme convention nomenclature designation EC 1.14.16.2. Unless indicated otherwise, the term "tyrosine hydroxylase", as used herein, refers to any of a variety of enzymes having the desired enzymatic activity. Tyrosine hydroxylases may be from a variety of organisms, both eukaryotic (mammalian or otherwise) and prokaryotic.

The term "polynucleotide encoding an enzyme in the synthesis of L-DOPA" refers to a nucleic acid sequence encoding an enzyme, or a subunit of an enzyme, involved in the synthesis of L-DOPA. In particularly preferred embodiments the polynucleotide of the invention is a polynucleotide encoding tyrosine hydroxylase. The term "polynucleotide encoding tyrosine hydroxylase", and variants of this term, refer not only to tyrosine hydroxylase genes isolated from natural sources (and cDNA derivatives thereof), but also to various non-naturally occurring polynucleotides encoding tyrosine hydroxylase, variants, functional derivatives and functional equivalents thereof. For example, a person of ordinary skill in the art may employ the degeneracy of the genetic code in conjunction with well known DNA synthesis and DNA manipulation techniques to produce a variety of polynucleotides encoding tyrosine hydroxylase. Similarly, a person of ordinary skill in the art may readily introduce one or more mutations in tyrosine hydroxylase polynucleotide coding sequence that do not abolish the activity of the enzyme (e.g., see U.S. Pat. No. 5,212,082). In some preferred embodiments of this invention, the polynucleotide encodes a tyrosine hydroxylase mutant (e.g., a truncated TH) which may be more active (see e.g., Moffat et al., (1997) Exp. Neurol. 144:69–73 and Wu et al., (1992) J. Biol. Chem. 267:25754–25758). Preferably, the polynucleotide encodes a tyrosine hydroxylase that is the same as a tyrosine hydroxylase found in the species to be treated by the subject methods of treating a patient. For example, when the patient to be treated is human, a polynucleotide encoding a human tyrosine hydroxylase may be used. However, tyrosine hydroxylase enzymes from other mammalian or non-mammalian sources may be used if they are functional in the human patient. Tyrosine hydroxylases from a variety of sources have been purified and the genes encoding such enzymes have been isolated. Tyrosine hydroxylases cloned from a number of organisms and the nucleic acid sequence coding tyrosine hydroxylases have been made publicly available. See, for example, O'Malley, et al., (1987) Biochemistry 26:6910–2614. Of course, polynucleotide encoding enzymatically active analogs of tyrosine kinase are useful as well.

The polynucleotide of the invention may comprise additional sequences useful for enhancing or regulating the expression of the encoded key enzyme. Such additional sequences include promoters, enhancers, regulatory protein-binding sites, polyadenylation sites, and the like. These additional regulatory sequences, enhancer sequences, etc., are selected so as to be functional in the mammal of interest. Promoter sequences, enhancer sequences, regulatory sequences, and the like, as well as methods of using such sequences to modify the expression of a gene of interest are well known to the person of ordinary skill in the art and can be found in among other places, *Gene Expression Technology: Methods in Enzymology, Vol.* 185 Goeddel, Ed. Academic Press, Inc., San Diego, Calif., (1991). The polynucleotide may be produced using conventional recombinant DNA techniques such as those described supra.

The polynucleotide of the present invention may be an expression vector. The expression vector may be a viral vector or a liposome that harbors the polynucleotide. Nonlimiting examples of viral vectors useful according to this aspect of the invention include lentivirus vectors, herpes simplex virus vectors, adenovirus vectors, adeno-associated virus vectors, various suitable retroviral vectors, pseudorabies virus vectors, alpha-herpes virus vectors, HIV-derived vectors, other neurotropic viral vectors and the like. A thorough review of viral vectors, particularly viral vectors suitable for modifying neural cells, and how to use such vectors in conjunction with the expression of polynucleotides of interest can be found in the book *Viral Vectors: Gene Therapy and Neuroscience Applications* Ed. Kaplitt and Loewy, Academic Press, San Diego, Calif., (1995). One useful viral vector for preparing the genetically modified mammalian host cells according to the method of the invention are retroviral vectors, such as the MFG vector. One nonlimiting example of a useful MFG vector is the MFG-S vector. A description of the MFG-S vector can be found, among other places, in co-pending U.S. patent application No. 08/252,710, filed Jun. 2, 1994, still pending, which is incorporated by reference to the extent that it does not directly contradict definitions of the subject invention provided herewith. Additional information on these retroviral vectors can be found, among other places in PCT Publications WO 92/07573, and WO 95/34669.

The polynucleotide according to the invention may be administered at a preselected target location by any known method of introduction. For example, a polynucleotide useful in the method of the present invention may be directly in vivo administered to cells which then produce the key enzyme involved in L-DOPA or dopamine production. Alternatively, host cells may be transfected, transduced or otherwise transformed ex vivo with a polynucleotide encoding the key enzyme and then grafted, or otherwise implanted in the mammal.

When a polynucleotide according to the invention is to be administered to the mammal directly, this may be accomplished via the direct injection of an expression vector including the polynucleotide at a preselected target location in the brain of the mammal (see e.g., Kordower et al., (1998) *Mov. Disorders* 13:383–393; Freed et al., (1992) *N.E.J. Med.* 327:1549–1555; and Widner et al., (1992) *N.E.J. Med* 327:1556–1563. Preferably, the patient to be treated is placed in a stereotaxis frame to pinpoint the target site in the brain for injection (for a discussion of the method see Paxinos, *The Rat Brain Stereotaxic Coordinates,* 512$^{nd}$ Ed. Academic Press, San Diego, Calif., (1987).

The "preselected target location" is a particular region in the brain of the mammal to be treated. In a preferred embodiment of the invention the preselected target location is a site in the mammal's caudate nucleus and putamen region of the brain. In a most preferred embodiment, the preselected target location is a site within the neostriatum of the brain of the mammal. Following identification of a suitable site of injection to reach the preselected target location, a solution containing the polynucleotide of the invention is injected at a controlled rate. Control of the rate of injection is effected using methods known in the art (e.g., see Mandel et al., (1998) *J. Neurosci.* 18:4271–4284.

The polynucleotide useful in the method of the invention may optionally be formulated with any of the well known pharmaceutically acceptable carriers or diluents, and may further contain other pharmacologically active agents. A representative example of a suitable carrier used in some of the embodiments of the invention is phosphate buffered saline (PBS).

The amount of polynucleotide to be directly injected into a patient is an amount sufficient to treat the patient, i.e., a therapeutically effective amount. The precise amount of polynucleotide administered to a patient will vary in accordance with a number of factors dependent upon the specific embodiment. Such factors include, but are not limited to, the specific virus from which the vector is derived and the specific promoter sequences used to drive gene expression. The term "therapeutically effective amount" is used to denote treatments at dosages effective to achieve the therapeutic result sought. Regulation of the level of L-DOPA and/or dopamine according to the invention is achieved by altering the amount of modulator administered at any given time. Accordingly, the total dosage of polynucleotide is highly variable since expression may be initiated, augmented, reduced or even suppressed externally at any given time. One of skill in the art will appreciate that therapeutically effective ranges of polynucleotide concentration include those concentrations resulting in the synthesis of therapeutically effective levels of L-DOPA and/or dopamine. In a particularly preferred embodiment, the therapeutically effective amount of polynucleotide is that sufficient to effectively introduce the polynucleotide in from about 500 to about $1 \times 10^6$ cells. In another embodiment of the invention, the therapeutically effective amount of polynucleotide is that sufficient to introduce the polynucleotide in from about 5000 cells to about $5 \times 10^5$ cells. In more preferred embodiments, the amount is that sufficient to introduce the polynucleotide in from about $1 \times 10^4$ cells to about $5 \times 10^4$ cells. In a most preferred embodiment, the amount is that sufficient to introduce the polynucleotide in from about $2 \times 10^4$ cells to about $3 \times 10^4$ cells.

One of skill will appreciate that the use of a vector capable of high expression may require considerably less vector than a weaker vector since high expression may be augmented by increasing the amount of modulator. Conversely, one may choose a low expression vector requiring a greater amount of vector to transform a sufficient number of cells to obtain therapeutically effective results. The polynucleotide encoding the key enzyme may alternatively be introduced ex vivo into a host cell and then by grafting, or otherwise implanting the cell, at the preselected target location in the mammal's (e.g., patient's) brain. Genetically modified host cells to be grafted in the mammal may be of a variety of species. Methods suitable to prepare genetically modified host cells and expression vectors are as described herein. The host cells are preferably of the same species as the patient being treated. More preferably, the host cells are derived directly from the patient to be treated so as to minimize immune system rejection problems. The cells may be encapsulated by a polymer so as to minimize unwanted response from the patient's immune system. The host cells may be of a variety of tissue and cell types, e.g., fibroblasts, hepatocytes, keratinocytes, endothelial cells and the like. Of particular interest is the use of host cells that are neural cells. The term "neural cell" as used herein, refers not only to neurons, but includes all cells of the mammalian central nervous system including astrocytes, microglial cells, etc.

The subject method of treating the patient comprises the step of administering a therapeutically effective amount of the genetically modified host cells to a patient (either human or animal) at a preselected target location. Genetically modified host cells may be administered by a variety of methods known to physicians including injections, surgical implantation, insertion through a canula, and the like. Usually, the genetically modified host cells are introduced into a site in a patient's brain that naturally contains such host cells. It should be understood that one of the advantages offered by the methods of the invention is that it allows controllable localized L-DOPA expression. Hence, one of skill wishing to localize L-DOPA production to the striatum may do so. As it will be apparent to those of skill, localized L-DOPA production may be clinically advantageous to avoid side effects (e.g., due to the delivery of L-DOPA to non-target regions).

A therapeutically effective amount of the genetically modified host cells includes that amount which reduces or stabilizes the detrimental symptoms of the disorder being treated as discussed infra. The exact amount of cells administered to a patient will vary in accordance with a number of factors, including the species of the host cell, the tissue from which the host cell is derived, the specific regulatory sequences in the genetic constructions used, body site of host cell implantation, the age and condition of the patient, the nature of the disease or disorder being treated, the stage of the disease or disorder, other medications being taken by the patient, and the like. The pharmacology and pharmacokinetics of dopamine and L-DOPA are well known. This pharmacological information can be used in conjunction with the measured dopamine and L-DOPA production levels of cultures of the subject genetically modified host cells in order to optimize the amount of cells administered.

Methods suitable to introduce the polynucleotide into the host cells to be grafted to the mammal are well known in the art. Nonlimiting representative methods include transfection using calcium phosphate precipitation, protoplast fusion, electroporation, lipofection (such as the use of cationic lipids, e.g., DOTMA, BRL, (Bethesda, Md.), transfection, packaged viral vectors, and the like.

Following introduction of the polynucleotide of the invention, either directly or indirectly by grafting as described above, the mammal is administered a modulator of the activity of the key enzyme. A "modulator" is a moiety capable of functioning as a cofactor in the conversion of L-tyrosine to L-DOPA (see FIG. 1). Modulators according to this aspect of the invention are pterins able to penetrate the blood-brain barrier after peripheral administration. Preferably, the modulator is tetrahydrobiopterin ($BH_4$), tetrahydropterin ($PH_4$), derivatives of $PH_4$, derivatives of $BH_4$. Nonlimiting examples of $PH_4$-derivatized modulators include 6-methyltetra-hydropterin ($6MPH_4$), 6,6-dimethyltetra-hydropterin ($6,6-MPH_4$), 6,7-dimethyltetra-hydropterin ($6,7-MPH_4$), and dihydrosepiapterin. Nonlimiting examples of $BH_4$-derivatized modulators include tetrahydroneopterin ($NH_4$), 6-cyclopropyltetrahydropterin ($6-CPH_4$), 6-phenyl-tetrahydropterin ($6-PPH_4$), 6-methoxymethyltetrahydropterin ($6-MMPH_4$), 7-tetrahdropiopterin ($7-BH_4$) and 6-ethoxymethyltetrahydropterin ($6-EMPH_4$). Such derivatives are described in the literature as for example in Levine et al., (1987) *J. Pharm. Exp. Ther.* 242:514–522, Davis et. al., (1992) *Proc. Natl. Acad. Sci.* USA 89:10109–10113, and Bigham et al., (1987) *J. Med. Chem.* 30:40–45.

Modulators according to the invention may optionally be formulated with any of the well known pharmaceutically acceptable carriers or diluents. This formulation may further contain one or more modulators or it may contain any other pharmacologically active agent. Hence, representative carriers according to this aspect of the invention include for example phosphate buffered saline (PBS).

As discussed supra, a crucial factor in the treatment of dopamine deficiencies is to establish and maintain localized, consistent, and uniform concentrations of dopamine in the brain, and to be able to modulate dopamine levels to meet an individual's requirements while minimizing the circulating levels of L-DOPA to non-target locations.

The inventors have discovered that to effectively moderate constant L-DOPA and dopamine production at a preselected target location, and to achieve more constant therapeutic effects, in addition to supplying an enzymatic moiety capable of catalyzing the conversion of L-tyrosine to L-DOPA at a preselected target location, it is necessary to supplement the enzymatic moiety with the cofactor $BH_4$ or a functional equivalent thereof. Preferably, continuously uniform levels of a modulator, which may be altered to meet the particular requirements of a patient, are effected using an externally controllable rate-controlled dosage release form, including for example, oral administration of coated pellets, slow-dissolving material released from a matrix, such as, for example, a transdermal drug delivery system or "patch," or by using an osmotic pump. For example, an osmotic infusion pump, controlled externally, i.e., from outside the body of the mammal, for example by telemetry, is used to establish and maintain externally adjusted levels of modulator in the mammal (see Ranade (1990) *J. Clin. Pharmacol.* 30:871–889). Nonlimiting representative examples of such pumps include SynchroMed pumps (Medtronic Inc., Minneapolis, Minn.) which is an implantable pump which can be fine-tuned to release customized dosages of modulator by adjusting the rate of flow of medication and time of delivery from outside the body via telemetry. One of skill in the field will appreciate that the ability to control the level of L-DOPA and of dopamine at a preselected target location provides a higher level of control and thus increased therapeutic efficacy, efficiency and safety for the treated mammal (e.g., patient).

The amount of modulator to be administered to a mammal at a preselected target site is an amount sufficient to treat the patient, i.e., a therapeutically effective amount. The precise amount of modulator administered to a patient will vary in accordance with a number of factors dependent upon the specific embodiment. Such factors include, but are not limited to, the preselected target location (e.g., the specific patient cells to be infected), the state of substantia nigra degeneration in the case of PD, the age and condition of the patient, and other medications being taken by the patient. The term "therapeutically effective amount" is used to denote treatments at dosages and for periods of time effective to achieve the therapeutic result sought. Furthermore, one of skill will appreciate that the therapeutically effective amount of the modulator administered to the mammal may be decreased or increased to fine tune and alter the amount of the L-DOPA effectively available in the mammal. The invention therefore provides a method to tailor the introduction/administration to the particular exigencies specific to a given patient.

As illustrated in the following examples, therapeutically effective ranges may be easily determined, for example empirically by starting at relatively low amounts and by step-wise increments with concurrent evaluations of the treated mammal to ascertain any changes as discussed infra.

Preferably, the modulator useful in the method of the invention is administered peripherally at a sufficient dosage to attain a modulator level in the blood serum sufficient to penetrate and affect, as desired, the preselected target location in the brain of the mammal. One of skill in the art will appreciate that the range of concentrations in the brain, of representative modulators, such as for example $BH_4$, necessary for TH activity approximate the known Km for this enzyme, i.e., in the range of 10–20 $\mu$M (see Levine et al., (1981) *Science* 214:919–921).

A practitioner will initially administer a relatively low amount of modulator to attain a concentration in the brain from about 5 $\mu$M to about 500 $\mu$M. In a particularly preferred example, the modulator is administered at a sufficient dosage to attain a concentration level from about 75 $\mu$M to about 425 $\mu$M. More preferably, the modulator is administered at a sufficient dosage to attain a concentration level from about 145 $\mu$M to about 355 $\mu$M. Preferably, the modulator is administered at a sufficient dosage to attain a concentration level from about 215 $\mu$M to about 285 $\mu$M.

In an embodiment of the invention the total dosage of modulator will range from about 2.9 $\mu$g to about 8.5 $\mu$g modulator per kg body weight. More preferably, the total dosage of modulator will range from about 4.3 $\mu$g to about 7.1 $\mu$g modulator per kg body weight. In a particularly preferred embodiment, the therapeutically effective amount of modulator will range from about 5 $\mu$g to about 6.4 $\mu$g modulator per kg body weight. One with skill in the art will appreciate that therapeutically effective ranges of modulator concentrations include those concentrations resulting in the synthesis of therapeutically effective levels of L-DOPA or dopamine in the particular mammal to be treated. Hence, it will be understood that the above ranges are based on animal experiments (described infra) using selected inbred specimen, which may therefore provide ranges of values that differ markedly from therapeutic values in other animals such as for example, humans. The skilled artisan will understand that the methods of the invention are to be used in concomitance with continuous clinical evaluations by a skilled practitioner of the treated mammal to inform subsequent steps. Hence, following the introduction of the polynucleotide encoding tyrosine hydroxylase or a functional equivalent thereof, and the peripheral administration of a modulator, the practitioner will evaluate any changes in the treated mammal. Such evaluation will aid in the determination of whether subsequent administration(s) of modulator is/are needed and, if applicable, to inform the practitioner's decision as to the appropriate increment or reduction of modulator necessary according to patient's tolerance until maximum benefit is reached.

Clinical changes relevant to assess the therapeutic effects of treatments according to the invention include reduction in the four major characteristic symptoms and signs of PD (bradykinesia, rigidity, resting tremor, and postural instability). These are based upon patient's symptoms and physician's observations.

The present invention also provides a method for the evaluation of the effects of varying concentration of L-DOPA in a preselected target location of the brain of a mammal. More specifically, the methods according to this second aspect of the invention provide the tools necessary for th e analysis of the neuroprotective potential and physiological effects of precisely regulated levels of L-DOPA in a preselected target location of the brain of a mammal. The methods according to this aspect of the invention are essentially a s described for the first aspect of the invention.

T he following examples illustrate the preferred modes of making and practicing the present invention, but are not meant to limit the scope of the invention since alternative methods may be utilized to obtain similar results.

EXAMPLE 1

Preparation of Animal Model

In order to exemplify the external modulation of striatal L-DOPA levels at a preselected target site in the brain of a mammal according to the invention by combining a gene therapy approach to supply a key enzyme in the synthesis of L-DOPA and an externally controllable modulator of the activity of such key enzyme, eighteen Harlan Sprague-Dawley, Indianapolis, Ind., rats with unilateral depletions of striatal dopamine by experimental lesion made as described in Schmidt et al., (1983) Acta Physiol. Scan. 522:19–28 were injected on the lesioned side with a vector encoding human tyrosine hydroxylase (see Example 2). An additional group of similarly lesioned rats received a vector encoding green fluorescent protein (GFP) (see Example 2) as a control for transduction. Several weeks after transduction, the tyrosine hydroxylase transduced rats were peripherally supplemented with representative modulators according to the invention (e.g., by subcutaneous osmotic minipumps filled with $MPH_4$, $BH_4$, or a vehicle solution). Harvested brain tissues were harvested and tissue samples taken for determination of striatal L-DOPA levels by standard HPLC.

EXAMPLE 2

Assembly of Retroviral Vectors

Lentiviral vectors were used to illustrate the introduction of a nucleic acid encoding tyrosine hydroxylase in a cell. One of skill in the art will appreciate that a variety of alternative vectors, including other retroviral vectors and liposomes described in the scientific literature (see for example, Robbins, *Gene Therapy Protocols*, Humana Press, Totowa, N.J. (1997) and Lemoine and Cooper, *Gene Therapy*, BIOS Scientific Publishers Limited, Oxford, U.K. (1996)) may be used instead. Lentiviral particles containing ribonucleic acid encoding human tyrosine hydroxylase (lenti-hTH) or GFP (lenti-GFP) from an internal CMV promoter were produced by transient transfection into 293T cells as described by Naldini et al., (1996) *Science* 272:263–267 with the following modifications. 5×10⁶ 293T cells were seeded in 10 cm dishes 24 hr prior to transfection in IMDM culture media (JRH Biosciences) with 10% PBS, penicillin (100 IU/ml) and streptomycin (100 $\mu$g/ml) in a 5% $CO_2$ incubator, and the culture medium was changed 2 hr prior to transfection. A total of 20 $\mu$g of plasmid DNA was used for the transfection of one dish: 3.5 $\mu$g of the envelope plasmid pMD.G; 6.5 $\mu$g of packaging plasmid; and 10 $\mu$g of transfer vector plasmid. The precipitate was formed by adding the plasmids to a final volume of 450 $\mu$l 0.1×TE (TE: 10 mM Tris pH 8.0, 1 mM EDTA) and 50 $\mu$l 2.5 M $CaCl_2$, mixing well, then adding dropwise 500 $\mu$l 2×HBS (281 mM NaCl, 100 mM HEPES, 1.5 mM $Na_2HPO_4$, pH=7.12) while vortexing, and immediately adding the precipitate to the cultures. The medium was replaced after 14–16 hrs and the conditioned medium was collected after 24 hr, cleared by low-speed centrifugation, and filtered through 0.22 $\mu$m cellulose acetate filters. Particles were concentrated by ultracentrifugation at 50,000×g for 140 min at 20° C. and resuspended in phosphate buffered saline (PBS) for injection. Particle concentration was estimated by Gag p24 antigen concentration by immunocapture assay (Alliance, DuPont-NEN. Boston, Mass.). Transduction activity was measured in vitro by infection of HeLa cells with serial dilutions of particles, and immunocytochemical staining of the cultures for tyrosine hydroxylase (TH vector) or FACS analysis for fluorescent cells (GFP vector) 3 days after infection. Vector titers were approximately $1 \times 10^9$ transducing unit/ml for the TH vector and $1 \times 10^9$ for the GFP vector.

EXAMPLE 3

Maintenance and Manipulation of Model Rats

Fischer 344 male rats weighing approximately 220 g were obtained from Harlan Sprague-Dawley (Indianapolis, Ind.), housed with access to ad libitum food and water on a 12 hr light/dark cycle and were maintained and treated in accordance with published NIH guidelines. All surgical procedures were performed with the rats under isofluorane gas anesthesia using aseptic procedures. After a rat was anesthetized in a "sleep box" it was placed in a small animal stereotaxic device (Kopf Instruments, Tujunga, Calif.) using the earbars which do not break the tympanic membrane. Prior to any particle injections, unilateral 6-OHDA lesions were performed with the rats under isoflurane anesthesia by stereotaxic injection of 4 $\mu$g/$\mu$l 6-OHDA HBr [calculated as free base, dissolved in 2 mg/ml ascorbate-saline] at two separate sites (Schmidt et al., (1983) *Acta Physiol. Scand.*, 522:19–28). All animals utilized in this experiment were pre-screened for robust amphetamine (2.0 mg/kg, 1 week after lesioning, mean total for rats in this experiment= 648±46/90 min) and apomorphine-induced rotational behavior (0.1 mg/kg, 3 times beginning 3 weeks after 6-OHDA injection, once per week, mean total for rats in this experiment for the third test=417±60/60 minutes). This lesion has reliably led to a greater than 98% depletion of DA in the striatum in animals which met this screening criteria. Rotational behavior was assessed using automated rotometers (Ungerstedt, Arbuthnott (1970) *Brain Res.*, 20:485–493). The rats were placed in the apparatus and allowed to habituate for between 5 and 10 min. After the habituation period, each rat was injected with the appropriate agonist. Net rotations were calculated as rotations in the inappropriate direction subtracted from rotations in the appropriate direction (clockwise for apomorphine-induced rotational behavior, counterclockwise for amphetamine-induced rotational behavior).

EXAMPLE 4

Intracerebral Injection of Lentiviral Vectors

After the rats were placed in the stereotaxic frame, 2 individual injections of 1 $\mu$l of lentiviral vector in PBS was injected into the striatum (AP +0.5, LAT −2.7, DV −5.5, −4.5, −3.5 and AP −0.5, LAT −3.2, DV 5.5, −4.5, −3.5 with the incisor bar set at −3.3 mm below the intra-aural line (Paxinos, Watson, *The Rat Brain in Stereotaxic Coordinates*, $512^{nd}$ Ed. Academic Press, San Diego, Calif., (1987)) through a 5 $\mu$l Hamilton syringe fitted with a 30 gauge beveled hypodermic needle over 2 minutes at a rate of 0.5 $\mu$l per minute. The rate of injection was precisely controlled by an injection system described previously (Mandel et al., (1998) *J. of Neurosci.* 18(11):4271–4284). During the injection the needle was slowly raised 1 mm in the dorsal direction every 20 seconds. One minute after the cessation of the injection the needle was retracted an additional 1 mm and then left in place for an additional 4 minutes before being slowly withdrawn from the brain.

EXAMPLE 5

Peripheral Continuous Administration of a Modulator

Twenty-three unilateral 6-OHDA lesioned animals were divided into 4 separate experimental groups statistically balanced for equality of pre-vector injection amphetamine- and apomorphine-induced rotational behavior prior to particle injection. Each group was randomly assigned to receive one of the following 2×1 $\mu$l intrastriatal vector injections as described above: lenti-hTH (n=17) or lenti-GFP (n=6) injections served as the control condition. Three weeks after the lentiviral vector injections, the animals were briefly anesthetized with isoflurane and the lenti-hTH injected rats were implanted with osmotic minipumps (Alza Corp, Palo Alto, Calif.) containing either 30 mg/ml 6-erythrotetrahydrobiopterin ($BH_4$, RBI, Natick, Mass.) in $dH_2O$ containing 2 mg/ml ascorbic acid (all solutions and the pumps were pretreated with argon gas to remove oxygen prior to loading for 30 seconds), an identical 30 mg/ml tetrahydropterin ($PH_4$, Sigma, St. Louis, Mo.) solution (n=6), vehicle ($dH_2O$+ascorbate, n=5), and the lenti-GFP injected rats received pumps containing either the $BH_4$ solution (n=3) or the $PH_4$ solution (n=3). The lenti-GFP group was treated as a single control group as it was later shown that there was no effect of the $BH_4$ or $PH_4$ administration. Three to 4 days after the minipump implantation the animals were injected (ip) with 30 mg/kg of the same solution as was present in their pumps. Ninety-minutes later each animal was injected with 75 mg/kg NSD-1015 (RBI) to block striatal 1-aromatic amino-acid decarboxylase activity to allow accurate measurement of striatal L-dihydroxyphenyl-alanine (L-DOPA) accumulation. One to two hours later the animals were sacrificed as described below.

EXAMPLE 6

Analysis of Treated Rats: Tissue Punching and Histology

Each animal was deeply anesthetized with ip pentobarbital and decapitated. Their brains were removed from the skull, placed in a brain slicer mold (Braintree, Mass.) and a 4 mm thick coronal slice at the level of the striatum was taken. The coronal brain slice was then placed on an ice-cold microscope slide and 2 mm diameter tissue punches were taken from the medial ventral striatum from identical location in both hemispheres. The remaining 4 mm thick coronal section was then immersion-fixed in 4% PFA by immersion for 24 hr, and then transferred into a 30% sucrose/PBS solution for 3–4 days until the slices sank to the bottom of their containers. The brains were then frozen on dry ice, and 40 $\mu$m thick coronal sections were cut on a sliding microtome. Sections were collected in micro-titre-well plates in series that contained a glycerin based anti-freeze solution, and they were kept at −30° C. until further processing. Immunochemical analysis was performed following general protocols described in the scientific literature. After several PBS rinses and an incubation in 3% hydrogen peroxide, the sections were placed in a 3% normal goat serum (Vector Laboratories, Burlingame, Calif.) for 30 minutes to block non-specific antigens]. The blocking step was followed by the primary antibody incubation which varied depending on the primary antibody. TH staining was carried out using a monoclonal anti-TH antibody (diluted in PBS with 1% NHS and 0.1% Triton X-100 in 1:1000 dilution) for 18 hr at room temperature.

EXAMPLE 7

Analysis of Treated Rats: HPLC Quantitation

The levels of L-DOPA, DA, and DOPAC in 20 μl samples were analyzed by reverse-phase HPLC using a C-18, 3 mm×150 mm Hypersil ODS (Keystone Scientific) column and an ESA Coulochem II electrochemical detector as described in the literature (see for example, Leff et al., (1998) *Exp. Neurol.*, 151:249–264). Factorial analysis of variance (ANOVA) was used to determine the probability of significant differences (a level was p<0.05). A hierarchical approach to simple-main effects for post hoc analyses as described by Kirk (Kirk, *Experimental Design: Procedures for the Behavioral Sciences,* Brooks/Cole, Ed., Belmont, Calif. (1968)) was followed. Measurement of L-DOPA from striatal tissue punches demonstrated that there was significantly more striatal L-DOPA accumulation in the lenti-hTH injected animals that received peripheral administration of either $BH_4$, the cofactor for TH, or the $PH_4$ analog, as compared to either the lenti-hTH injected animals which did not receive any cofactor treatment or the co-factor treated lenti-GFP controls [F(1,19)=12.5, p=0.002, see FIG. 1]. There was no effect of co-factor treatment without hTH gene transfer which was demonstrated by the lack of difference between the lenti-hTH injected animals that received no co-factor as compared to the lenti-GFP injected animals which did receive peripheral cofactor treatment [F(1,19)= 0.02, p=0.89]. Furthermore, peripheral administration of $BH_4$ or $PH_4$ produced equivalent amounts of increased striatal L-DOPA accumulation in 6-OHDA lesioned rats [F(1,19)=1.18, p=0.29] which was 15–20% of the L-DOPA accumulation measured on the intact side.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A method for increasing brain L-DOPA levels in a mammal, comprising the steps of:
   (a) introducing into a preselected location of the brain of the mammal a polynucleotide encoding tyrosine hydroxylase or a functional derivative of tyrosine hydroxylase that converts tyrosine to L-DOPA; and
   (b) peripherally administering a modulator of the activity of the tyrosine hydroxylase or functional derivative of tyrosine hydroxylase at continuously regulated levels, wherein the administration of the modulator results in increasing brain L-DOPA levels in the mammal.

2. The method of claim 1, wherein the polynucleotide is a DNA.

3. The method of claim 2, wherein the modulator is selected from the group consisting of $BH_4$, $PH_4$, 6-$MPH_4$, 6,6-$MPH_4$, 6,7-$MPH_4$, dihydrosepiapterin, 7-$BH_4$, $NH_4$, 6-$CPH_4$, 6-$PPH_4$, 6-$MMPH_4$, and 6-$EMPH_4$.

4. The method of claim 2, wherein the modulator is $BH_4$.

5. The method of claim 2, wherein the modulator is $PH_4$.

6. The method of claim 1, wherein the mammal is a human suffering from a dopamine deficiency.

7. The method of claim 6, wherein the dopamine deficiency is Parkinson's disease.

8. The method of claim 1, wherein the polynucleotide encoding the tyrosine hydroxylase or functional derivative of tyrosine hydroxylase is introduced via injection into the preselected target location of the brain of the mammal.

9. The method of claim 1, wherein the preselected target location in the brain of the mammal is the neostriatum.

10. The method of claim 1, wherein the polynucleotide encoding the tyrosine hydroxylase or functional derivative of tyrosine hydroxylase is an expression vector.

11. The method of claim 10, wherein the expression vector is a viral vector.

12. The method of claim 11, wherein the viral vector is selected from the group consisting of lentivirus vectors, herpes simplex virus vectors, adenovirus vectors, adeno-associated virus vectors, retroviral vectors, pseudorabies virus vectors, alpha-herpes virus vectors, HIV-derived vectors, and other neurotropic viral vectors.

13. The method of claim 1, wherein the modulator is administered orally to the mammal.

14. The method of claim 1, wherein the modulator is administered subcutaneously or intravenously to the mammal.

15. The method of claim 14, wherein the modulator is administered by an osmotic minipump.

* * * * *